US006299925B1

(12) United States Patent
Xiong et al.

(10) Patent No.: US 6,299,925 B1
(45) Date of Patent: Oct. 9, 2001

(54) EFFERVESCENT GREEN TEA EXTRACT FORMULATION

(75) Inventors: Weihong Xiong; Danyi Quan; Dinesh C. Patel, all of Salt Lake City, UT (US)

(73) Assignee: XEL Herbaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 09/342,787

(22) Filed: Jun. 29, 1999

(51) Int. Cl.$^{7}$ .......... A23F 3/00

(52) U.S. Cl. .......... 426/597; 426/591; 426/285; 426/477

(58) Field of Search .......... 426/591, 597, 426/285, 477

(56) References Cited

U.S. PATENT DOCUMENTS

| | | | |
|---|---|---|---|
| 3,653,914 | * | 4/1972 | Schmitt . |
| 3,660,107 | | 5/1972 | Mayer . |
| 4,004,036 | | 1/1977 | Schmitt . |
| 4,009,292 | | 2/1977 | Finucane . |
| 4,440,796 | | 4/1984 | Lunder et al. . |
| 4,552,771 | * | 11/1985 | Fulberth et al. . |
| 4,897,257 | * | 1/1990 | Nishhikawa et al. . |
| 5,171,571 | | 12/1992 | Stephan et al. . |
| 5,543,165 | * | 8/1996 | Hill . |
| 5,837,286 | | 11/1998 | Pandya et al. . |

FOREIGN PATENT DOCUMENTS

| | | |
|---|---|---|
| 0919 227 A1 | 6/1999 | (EP) . |
| 0922 450 A1 | 6/1999 | (EP) . |

OTHER PUBLICATIONS

Database Abstract. Derwent–Acc–No.: 1997–544143. For JP 09262078 published Oct. 7, 1997.*

Database Abstract. Derwent Acc No.: 1997–424658 for ES 21222894, 1997.*

Database Abstract. Derwent Acc. No. 1998–488335 for JP10210932A, 1998.*

The Pharmacological Basis of Therapeutics (Fourth Edition) The Macmillan Company pp. 828 to 830 1970.

Ask the Experts (Women's Health) Natural Health p. 50 Jun. 1999.

Morinda USA: The Morinda Story p. 1 and 2 Date not available.

Kombucha Tea Ref.: The Miracle Fun . . . y Harald Tietze—Cygnus Book Club @ www.cygnus–books.co.uk 1995.

* cited by examiner

*Primary Examiner*—Anthony J. Weier
(74) *Attorney, Agent, or Firm*—Thorpe North & Western, LLP

(57) ABSTRACT

A solid state water soluble formulation in granular or tablet form is provided. The formulation is a natural products formulation containing a green tea plant extract in combination with other ingredients which create an effervescent liquid composition upon dispensing the formulation in a liquid. The liquid form of administration, as well as the effervescent properties of the dissolved formulation increase bioavailability of the advantageous components of the green tea plants such as Polyphenols, by increasing absorption speed and amount in the human body. The formulation may include additional components such as, other plant extracts, vitamins, ionic minerals, and other substances purported to be of a health benefit.

36 Claims, No Drawings

EFFERVESCENT GREEN TEA EXTRACT FORMULATION

THE FIELD OF THE INVENTION

The present invention relates generally to a green tea extract formulation which maximizes release and delivery of a therapeutic extract contained therein to the human body. More particularly, it concerns an effervescent tablet containing a green tea extract which is dispensed in a liquid for consumption.

BACKGROUND OF THE INVENTION

Nearly 4,000 years ago, the people of the far east recognized many general health and refreshment benefits from the consumption of green tea. Such recognition has led to a wide spread use of tea which has even gained cultural status and significance in many areas of the world. However, the specific health benefits of green tea consumption have been little understood until recently.

Today, scientific evidence has linked certain positive health effects, including anti-cancer and anti-heart disease effects, to various components of green tea. Specifically, positive effects in fending off cancer, heart disease, and other health benefits come from the green tea components of Catechins polyphenols, Polysaccharides, Flavonoids, Vitamin B complex, Vitamin C, Vitamin E, r-Amino Butyric Acid, and Fluoride. Polyphenols, otherwise known as catechins, and particularly epigallocatechin gallate (EGCG) have shown anti-microbial, anti-mutagenic, and anti-carcinogenic effects when administered in significant doses.

Although there are several types of tea, only tea prepared from the green tea plant *Camillia Sinesis*, dried without fermentation, contains the highest content of catechins. Other teas which are derived from the green tea plant, such as black tea and oolong tea lose some of their polyphenols anti-oxidant potency during their fermentation process. Therefore, these types of tea are somewhat less desirable to consume for their health benefits.

Conventional tea preparation, by seeping the tea plant in hot water, extracts only the water soluble tea components. Some of the most valuable components of green tea plants are actually water insoluble. Therefore, in order to receive the full health benefits offered by the tea, an extract which will allow the release of both water and alcohol soluble elements is necessary.

Newer technologies allow extraction of key green tea plant ingredients. Often such an extract is combined into a formulation with additional substances such as vitamins, essential minerals, and other items which are purported to be of a health benefit. Such formulations can be produced in different dosage forms, such as capsules and tablets.

Unfortunately, capsules or tablets can be difficult to administer to elderly people and children. Additionally, solid or crystalline dosage forms can require a significant amount of time for absorption by the body. This poor bioavailability often results in much of the dosage amount passing though the body unabsorbed.

In addition to green tea, many other natural products, such as herbs, fruits, and vegetables, and other botanicals have been known to impart positive, refreshing, therapeutic, and medicinal effects when consumed in sufficient quantities. To this end, herbal teas, juices, and other beverages have been prepared from selected items. As with green tea, the basic problem in the past has been the need to identify, and extract the beneficial components of each item into a form sufficient to achieve the desired therapeutic and beneficial effects within a reasonable daily dosage. Here too, the conventional dosage forms such as capsules and tablets suffer from the same disadvantages as the traditional green tea products detailed above.

The concept of effervescence has long been known in the art of beverage making for the pleasant characteristics it imparts. Soda pop and other flavored beverages have been known to be produced from a tablet which combines a desired flavorant ingredient with effervescence causing ingredients. For many years, only beverages having a strong flavor such as a citrus, or grape flavor could be utilized by such a tablet, because of the strong bitter alkaline taste which is produced by the normal combination of acidic and carbonate effervescence causing ingredients.

However, one reference discloses an effervescent couple which when applied in a proper ratio does not cause such a bitter alkaline taste, and is therefore useful to produce beverages having a mild flavor such as coffee, tea, and chocolate. This reference is U.S. Pat. No. 3,660,107 to Mayer. (hereinafter "Mayer")

The effervescent "couple," or composition taught by Mayer includes tartaric acid, citric acid, and sodium bicarbonate combined in a 2:1:4 ratio. Apparently, this particular ratio, and only this particular ratio, is capable of producing an effervescence effect when dissolved in water without producing the undesired metal alkaline taste. Mayer contemplates using the effervescent couple with a solid flavorant such as freeze dried coffee extract for the formation of the desired beverage.

Unfortunately, the tartrate ion is a well known cathartic, which when delivered in substantial doses could cause great gastrointestinal discomfort and purging. Additionally, if sufficient quantities of tartrate ion are allowed to enter the circulatory system, renal damage may result.

In addition to the pleasant effects that effervescence adds to a beverage, it is also thought to be useful in speeding the body's absorption of components associated therewith. This effect has been made famous by Alka-seltzer® brand medicines. Analgesics, cold medicines, and even anti-acids have been used in combination with an effervescent compound in order to speed relief to a suffering individual.

In view of the foregoing, a natural product formulation containing a concentrated green tea extract, in a final delivery form which is both easily administered, and which increases bioavailability is desirable. Further, a natural product formulation containing a concentrated green tea extract which increases absorption rate, and therefore bioavailability is highly desirable. Finally, a natural product formulation containing a concentrated green tea extract in combination with components capable of forming an effervescent composition when combined with a liquid is most desirable.

OBJECTS AND SUMMARY OF THE INVENTION

It is therefore an object of the present invention to provide a natural product formulation containing a concentrated green tea extract that is capable of being administered in a liquid form.

It is an additional object of the present invention, to provide a natural product formulation containing a concentrated green tea extract which increases the formulation's absorption rate, and therefore bioavailability.

It is a further object of the present invention to provide a natural product formulation containing a concentrated green tea extract having ingredients which allow the formulation to produce an effervescent composition when the formulation is combined with a liquid.

The above objects and others not specifically recited are realized in a specific illustrative embodiment of a solid state water soluble formulation containing by weight, about 10 to 50 percent of a green tea plant extract. Other extracts from plants such as herbal plants, fruits, and vegetables may additionally be added, typically in an amount of about 5 to about 50 percent by weight. However, the amount of total green tea plant and other plant extracts must not exceed 80 percent by weight of the total formulation, in order to allow addition of the below listed ingredients in adequate amounts.

The formulation further contains about 5 to 30 percent by weight volume of a carbonate salt, preferably sodium bicarbonate, and about 10 to 45 percent by weight volume of an acidic material, preferably citric acid. When dispensed in water, these components react to create effervescence. Additionally, the formulation includes about 1 to 10 percent by weight volume of a lubricant, preferably a polyethylene glycol with an average molecular weight of 6000, and about 1 to 10 percent of a binding agent, or binder, which is preferably polyvinyl pyrrolidone. Finally, the formulation of the present invention includes about 0.1 to 3 percent by weight volume of a flavor agent, and may optionally contain about 0.1 to 5 percent by weight volume of a sweetening agent such as sugar, aspartame, saccharin, or any other natural sweetener.

The solid state water soluble formulation of the present invention generally takes the form of granules or a tablet. The most common way of preparing such a dosage form is to combine the specific desired amount of each of the above listed ingredients, and mix them thoroughly. After the ingredients have been sufficiently mixed, they are compressed into either granular or a tablet form.

Finally, the formulation is used by dispensing it in water, and waiting until it is substantially, disbursed or dissolved. By allowing the formulation to become substantially disbursed or dissolved, the beneficial extract components are unlocked and become more available to the body upon consumption. Additionally, the effervescent action of the formulation further agitates and unlocks the beneficial extracts contained therein. Therefore, such a delivery form creates a higher absorption rate of the extracts upon consumption. For example, a green tea extract may be prepared which has a polyphenol content of about 5 to about 99 percent by weight.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

DETAILED DESCRIPTION

For the purposes of promoting an understanding of the principles in accordance with the invention, reference will now be made to the preferred embodiment of the invention specific language will be used to describe the same. It will nevertheless be understood that no limitation of the scope of the invention is thereby intended. Any alterations and further modifications of the illustrated product, and any additional applications of the principles of the invention as illustrated herein, which would normally occur to one skilled in the relevant art and in possession of this disclosure, are to be considered within the scope of the invention claimed.

The preferred embodiment is chosen and described in order to best explain the principles of the invention and its practical application. The following description is intended to enable others skilled in the art to best utilize the invention in various embodiments and with various modifications as are suited to the particular use contemplated.

Applicant has discovered that the beneficial and medicinal properties imparted by green tea plants are greatly increased, when a concentrated extract thereof is prepared and delivered to the body in an effervescent solution. Specifically, the consumption quantity necessary to achieve the desired positive effect is greatly reduced by extracting and concentrating the desired substances from the green tea plant and combining them into a solid state formulation with other ingredients. Additionally, the bioavailabilty of the desired substances is greatly increased because of a more rapid absorption by the body.

The dosage form most advantageous is an effervescent tablet or granules which can be dispensed or deployed in a liquid to release the desired extract agents, such as polyphenols (catechins), in the formulation. The liquid dosage form speeds the absorption rate of the desired extract in the body, because the extract has already been separated from the other plant components and distributed throughout the volume of liquid. Further, by including effervescence causing ingredients, an effervescent action will be created upon the deployment of the formulation in a liquid. Such effervescent action creates additional turbulence in the liquid composition, further unlocking the desired extracts by separating them in solution. Therefore, the extracts are more exposed to the digestive forces inside the body, and absorbed at a much greater rate.

The solid state of the formulation is preferred because of its convenience in use, travel, and packaging. Further, the solid state formulation tends to increase stability over time for the desired extracts, thus slowing the rate at which they decompose and lose their desirability. Such stability is extremely important for manufacture, sale, and storage purposes.

Typically, in production, a desired extract is selected and prepared (i.e. extracted from the plant and concentrated) based upon the positive effects it is reported to impart. The extraction and concentrations may be performed by any method well known in the relevant art of making concentrated extracts from natural products such as water, alcohol, and solvent based extractions with accompanying concentration of the extracted material. Additionally extraction processes may be custom suited to extract specific desirable elements requiring a special extraction technique in order to extract them from the plant.

Next, the concentrated extract is combined into a solid state formulation by mixing it with a lubricant such as a polyethylene glycol 6000, and a binding agent such as polyvinyl pyrrolidone. Although, polyethylene glycol 6000 is the preferred lubricant, a wide range of known lubricants such as sodium benzoate, sodium lauryl sulfate, and other polyethylene glycols in the with an average weight in the range of 200 to 9000, are suitable for use in the formulation. Additionally, even though polyvinyl pyrrolidone is the preferred binding agent, many other known binders known in the relevant art may be used equally as well. Examples of such binders include, but are not limited to: starches, gelatins, lactose, mannitol, acacia, cabomer, carboxymethyl celluslose sodium, dextrin, guar gum, hydroxyethyl cellulose, hydroxypropyl cellulose, hydroxypropylmethyl cellulose, lactose, liquid glucose, maltodextrin, methylcellulose, polymethacrylates, having a molecular weight range from about 2,500 to 3,000,000 and their equivalents.

Next, in order to create the desired effervescent action upon delivery of the formulation into a liquid, an effervescence causing ingredient, or combination of ingredients are added to the mixture. In a preferred embodiment, a carbonate salt, such as sodium bicarbonate is added to react with a pharmaceutically acceptable acid to create the effervescence. Acceptable carbonate salts include, sodium carbonate, potassium carbonate, sodium bicarbonate, potassium bicarbonate, sodium glycine carbonate, and their equivalents. Additionally, pharmaceutically acceptable acids include food acids, acid anhydrides, acid salts, and equivalents thereof which are not know to produce an adverse health effect, when consumed in significant quantities. In a preferred embodiment, sodium bicarbonate is the carbonate salt, and anhydrous citric acid is the acid material.

In addition to the afore mentioned ingredients, other ingredients may be added to the mixture before it is ultimately shaped into the final dosage form. For example, flavoring agents, and sweetening agents. Flavoring agents may be chosen based upon the desired flavor for the beverage, and are nearly limitless in possibility. Sweetening agents may also be any type of general sweetening agent such as sugar, saccharin, aspartame, or other natural sweeteners.

Once all of the desired ingredients are present and thoroughly mixed by an appropriate method, the decision as to the formulation's final dosage form must be decided upon. Generally, either a tablet or granular form is most desirable. Therefore, the formulation is taken and compressed into the dosage form and amount decided upon by any common method known to those skilled in the art of tablet and granule production.

In use, the formulation is removed from its packaging material, and dispensed into a liquid such as water. The normal dosage unit of formulation is from about 1 gram to about 8 grams, and may be dispensed in any suitable volume of water. However, to ensure that consumption of the entire dosage amount is achieved, the volume of liquid should be estimated at about 0.6 to 1 cup, or from about 4 to about 8 ounces per dosage unit. Once the formulation has become substantially dissolved or disbursed in the liquid it is orally consumed.

The present invention primarily contemplates the production of a solid state water soluble formulation which incorporates a concentrated green tea plant extract Additionally, extracts from herbal plants, fruits, and vegetables which impart some therapeutic, positive, beneficial, or medicinal effect may be used.

Specific green tea plant formulations and blends well known and considered for incorporation into the present invention include, but are not limited to: Chinese green teas such as Lung Ching, Gunpowder, Jasmine, and Pu-erh teas; Japanese green teas such as Sencha, Kukicha, Genmaiha, Macha, Konacha, Hojicaha, Bancha, and Gykuro teas; Indian green teas such as Makaibari estate green tea; and Sri Lanka green teas such as Koslande green tea. Specific black tea formulations and blends well known and considered for incorporation into the present invention include, but are not limited to: Chinese black teas such as Labsand Souchong, and Keemun teas; Indian black teas such as Assam, Darjeeling, Nilgiri, and Orissa teas; African black teas such as Kenya, Malawi, Zimbabwe, and Yooibos teas; and Sri Lanka black teas such as Ceylon teas. Specific oolong tea formulations and blends well known and considered for incorporation into the present invention include, but are not limited to: Chinese oolong teas, and Darjeeling oolong teas. Finally, specific formulations of white tea well known and considered for incorporation into the present invention include, but are not limited to: Chinese white tea such as Pai Mu Tan, and Sow Me teas. Other true teas so qualified, but not specifically mentioned such as Chinese White tea may be utilized as equally as well for their specific health benefits. Generally, the polyphenol content in a prepared concentrated green tea extract may be from about 5 to about 99 percent by weight.

In addition to the selected plant extract ingredients, additional health proffering ingredients may be added. For example, vitamins either water soluble or oil soluble may be added. Water soluble vitamins specifically contemplated by the present invention include, but are not limited to: vitamin $B_1$, $B_2$, $B_3$, $B_5$, B6, $B_{12}$, $B_{15}$, $B_{17}$, biotin, choline, folic acid, inositol, para-aminobenzoic acid (PABA), vitamin C, and vitamin P. Additionally, oil soluble vitamins include, but are not limited to: vitamin A, vitamin D, vitamin E, and vitamin K.

Other health imparting substances which may be combined with the desired extract in the formulation of the present invention include amino acids, ionic minerals, and naturally occurring anti-oxidants. The amino acids contemplated include: alanine, arginine, carnitine, gamma-aminobutyric acid (GABA), glutamine, glycine, histidine, lysine, methionine, N-acetyl cysteine, ornithine, phenylalanine, taurine, tyrosine, and valine, but are not limited thereto. Additionally, the ionic minerals contemplated by the present invention for inclusion in an embodiment of the formulation include both anions and cations. Finally, the naturally occurring antioxidants contemplated for the formulation of the present invention include: grape seed, beta-carotene, and co-enzyme Q10, but are not limited thereto.

The range of possible plant extracts that can be concentrated and incorporated into the solid state water soluble formulation of the present invention are vast. Therefore, for the purpose of more clearly defining and promoting and understanding of the present invention, the following definitions are provided. The term "green tea plant" is meant to include all strains and hybrids of the *Camellia Sinesis* plant, and plants significantly related to it, grown anywhere in the world, which are used to make tea, including blends, mixtures, and combinations of such strains and relatives. Further included are blends mixtures, and combinations of such strains and relatives after various treatments such as fermentation have been applied to each. Additionally, as used herein, the term "herbal extract," is meant to include an extract from any herb or botanical, or part thereof, including flower, fruit, seed, peel, leaf, root, and bark, imparting a therapeutic, medicinal, beneficial, or positive property. As used herein, the term "pharmaceutically acceptable acid" is meant to include any acid that does not produce an negative effect on the body, when consumed in a quantity necessary for producing a suitable effervescent reaction for a beverage utilizing such a reaction to expedite delivery of a therapeutic, medicinal, beneficial, or positive substance. Finally, as used herein, the term "noni fruit" is used to mean the fruit of the Morinda Citrifolia plant and all strains, hybrids, or relatives thereof, found and cultivated in various geographic locals around the earth, including Hawaii, Tahiti, Samoa, and mainland China.

The following examples are illustrative of the different embodiments of the formulation of the present invention.

They are representative as to typical amounts of each ingredient, and of different possible combinations of ingredients, but act in no way as a limitation thereof.

EXAMPLE I

| Formulation | Composition (%, w/w) |
| --- | --- |
| Green tea extracts* | 10–50 |
| Sodium bicarbonate | 5–30 |
| Anhydrous citric acid | 10–45 |
| Polyethylene glycol 6000 | 1–10 |
| Polyvinyl pyrrolidone | 1–10 |
| Flavor agent | 0.1–3 |

*Concentrated green tea extracts can be selected from the regular extracts (with caffeine), decaffeinated green tea extracts, organic green tea extracts, and green tea extracts containing a different content of polyphenols. Additionally, green tea extracts can be unfermented, or fermented.

EXAMPLE II

| Formulation | Composition (%, w/w) |
| --- | --- |
| Green tea extracts | 10–50 |
| Vitamins* | 1–10 |
| Sodium bicarbonate | 5–30 |
| Anhydrous citric acid | 10–45 |
| Polyethylene glycol 6000 | 1–10 |
| Polyvinyl pyrrolidone | 1–10 |
| Flavor agent | 0.1–3 |

*One or more vitamins can be selected form either water soluble (vitamin $B_1$, $B_2$, $B_3$, $B_5$, $B_6$, $B_{12}$, $B_{13}$, $B_{15}$, $B_{17}$, biotin, choline, folic acid, inositol, PABA, vitamin C, and vitamin P) or oil soluble vitamins (vitamins A, D, E and K).

EXAMPLE III

| Formulation | Composition (%, w/w) |
| --- | --- |
| Green tea extracts | 10–50 |
| Amino acids* | 1–10 |
| Sodium bicarbonate | 5–30 |
| Anhydrous citric acid | 10–45 |
| Polyethylene glycol 6000 | 1–10 |
| Polyvinyl pyrrolidone | 1–10 |
| Flavor agent | 0.1–3 |

*Amino acids are selected from but not limited to alanine, arginine, carnitine, GABA, glutamine, glycine, histidine, lysine, methionine, N-acetyl cysteine, ornithine, phenylalanine, taurine, tyrosine, and valine.

EXAMPLE IV

| Formulation | Composition (%, w/w) |
| --- | --- |
| Green tea extracts | 10–50 |
| Ionic minerals* | 1–10 |
| Sodium bicarbonate | 5–30 |
| Anhydrous citric acid | 10–45 |
| Polyethylene glycol 6000 | 1–10 |
| Polyvinyl pyrrolidone | 1–10 |
| Flavor agent | 0.1–3 |

*Ionic minerals (both cations and anions) are from natural sources.

EXAMPLE V

| Formulation | Composition (%, w/w) |
| --- | --- |
| Green tea extracts | 10–50 |
| Herb/botanical extracts* | 5–50 |
| Sodium bicarbonate | 5–30 |
| Anhydrous citric acid | 10–45 |
| Polyethylene glycol 6000 | 1–10 |
| Polyvinyl pyrrolidone | 1–10 |
| Flavor agent | 0.1–3 |
| Sweetening agent | 0.1–5 |

*Herbal/botanical extracts are made from all kinds of herb and botanic sources and formulated based on their therapeutic function, for example, anti-flu, bone/joint, brain function, cardiovascular, circulatory, diet, depression, digestion, energy, eye vision, general health, immune system, liver, men's health respiratory, rest, urinary tract, women's health, etc. For example, extracts can be selected from, but not limited to, Ginseng, Ginko Biloba, Dong Quai, Hawthorn berry, St. John's Wort, Saw Palmetto, Kava Kava, Rose Hips, Echinacea, Licorice Root, Grape seed, Chammomile, Sea Buckthorn, Aloe Vera, Cinnamon Bark, Cordyceps, Ho Shou Wu, Dandelion, Gynostemma, mushroom, Notginseng, Dan Shen, and mixtures thereof.

EXAMPLE VI

| Formulation | Composition (%, w/w) |
| --- | --- |
| Green tea extracts | 10–50 |
| Natural anti-oxidants* | 1–10 |
| Sodium bicarbonate | 5–30 |
| Anhydrous citric acid | 10–45 |
| Polyethylene glycol 6000 | 1–10 |
| Polyvinyl pyrrolidone | 1–10 |
| Flavor agent | 0.1–3 |

*Anti-oxidant agents from natural sources can be selected from but not limited to Grape seed, beta-carotene, co-enzyme Q-10, etc.

EXAMPLE VII

| Formulation | Composition (%, w/w) |
| --- | --- |
| Green tea extracts | 10–50 |
| Fruit extracts* | 5–50 |
| Sodium bicarbonate | 5–30 |
| Anhydrous citric acid | 10–45 |
| Polyethylene glycol 6000 | 1–10 |
| Polyvinyl pyrrolidone | 1–10 |
| Flavor agent | 0.1–3 |

*Fruit extracts can be selected from, but not limited to Apple, Apricot, Banana, Blue berry, Cranberry, Cherry, Fig, Grape, Grapefruits, Hawthorn berry, Huckleberry, Kiwi fruit, Kumquat, Lemon, Lime, Mango, Melon, Nectarine, Noni fruit, Orange, Papaya, Peach, Pear, Persimmon, Pineapple, Plum, Pomegranate, Raspberry, Strawberry, Tangerine, Watermelon.

EXAMPLE VIII

| Formulation | Composition (%, w/w) |
| --- | --- |
| Green tea extracts | 10–50 |
| Vegetable extracts* | 5–50 |
| Sodium bicarbonate | 5–30 |
| Anhydrous citric acid | 10–45 |
| Polyethylene glycol 6000 | 1–10 |

-continued

| Formulation | Composition (%, w/w) |
|---|---|
| Polyvinyl pyrrolidone | 1–10 |
| Flavor agent | 0.1–3 |

*Vegetable extracts are selected from but not limited to Artichoke, Avocado, Asparagus, Beans, Bell Pepper, Broccoli, Brussels Sprout, Cabbage, Cauliflower, Carrot, Celery, Cucumber, Eggplant, green bean, Lettuce, Onion, Parsley, Pea, Potato, Pumpkin, Radish, Radicchio, Rhubarb, Spinach, Tomato, Zucchini.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been fully described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A solid state water soluble formulation comprising in percentage by weight:

a) about 10 to 50 percent of a concentrated green tea plant extract, having a polyphenol content of from about 5 to about 99 percent by weight;

b) about 5 to 30 percent of a carbonate salt;

c) about 10 to 45 percent of a pharmaceutically acceptable acid;

d) about 1 to 10 percent of a lubricant;

e) about 1 to 10 percent of a binding agent; and, f)1 about 0.1 to 3 percent of a flavor agent; such that when dispensed in water, said solid state formulation, forms an effervescent composition for consumption.

2. The solid state water soluble formulation of claim 1, wherein said green tea plant extract is unfermented.

3. The solid state water soluble formulation of claim 1 wherein said green tea plant extract is fermented.

4. The solid state water soluble formulation of claim 1, wherein said green tea plant extract is decaffeinated.

5. The solid state water soluble formulation of claim 1, wherein said green tea plant extract contains caffeine.

6. The solid state water soluble formulation of claim 1, wherein said polyphenol comprises epigallocatechin gallate (EGCG).

7. The solid state water soluble formulation of claim 1, further comprising at least one vitamin in an amount of about 1 to 10 percent by weight.

8. The solid state water soluble formulation of claim 7, wherein said at least one vitamin ingredient is a water soluble vitamin.

9. The solid state water soluble formulation of claim 8, wherein said at least one water soluble vitamin is a member selected from the group consisting of: Vitamin $B_1$, $B_2$, $B_3$, $B_5$, B6, $B_{12}$, $B_{13}$, $B_{15}$, $B_{17}$, Biotin, Choline, Folic acid, Inositol, Para-Aminobenzoic Acid, Vitamin C, and Vitamin P, and mixtures thereof.

10. The solid state water soluble formulation of claim 9, wherein said at least one vitamin is an oil soluble vitamin.

11. The solid state water soluble formulation of claim 10, wherein said oil soluble vitamin is a member selected from the group consisting of: Vitamin A, Vitamin D, Vitamin E, Vitamin K, and mixtures thereof.

12. The solid state water soluble formulation of claim 1, further comprising at least one amino acid in an amount of about 1 to 10 percent by weight.

13. The solid state water soluble formulation of claim 12, wherein said at least one amino acid is a member selected from the group consisting of: alanine, arginine, carnitine, gamma-aminobutyric acid, glutamine, glycine, histidine, lysine, methionine, N-acetyl cysteine, ornithine, phenylalanine, taurine, tyrosine, valine, and mixtures thereof.

14. The solid state water soluble formulation of claim 1, further comprising at least one ionic mineral in an amount of about 1 to 10 percent by weight.

15. The solid state water soluble formulation of claim 14, wherein said at least one ionic mineral is a cation.

16. The solid state water soluble formulation of claim 14, wherein said at least one ionic mineral is an anion.

17. The solid state water soluble formulation of claim 1, further comprising at least one herbal extract in an amount of about 5 to 50 percent by weight, with the proviso that any combined amount of herbal extract and green tea extract may not exceed 80 percent by weight of the total formulation.

18. The solid state water soluble formulation of claim 17, wherein said at least one herbal extract is a member selected from the group consisting of: Ginseng, Ginko Biloba, Dong Quai, Hawthorn berry, St. John's Wort, Saw Palmetto, Kava Kava, Rose Hips, Echinacea, Licorice Root, Grape seed, Chammomile, Sea Buckthorn, Aloe Vera, Cinnamon Bark, Cordyceps, Ho Shou Wu, Dandelion, Gynostemma, mushroom, Notginseng, Dan Shen, and mixtures thereof.

19. The solid state water soluble formulation of claim 18, wherein said herbal plant extract is concentrated.

20. The solid state water soluble formulation of claim 1, further comprising at least one naturally occurring antioxidant in an amount of about 1 to 10 percent by weight.

21. The solid state water soluble formulation of claim 20, wherein said at least one naturally occurring antioxidant is a member selected from the group consisting of: Grape seed, Beta-carotene, Co-enzyme Q-10, and mixtures thereof.

22. The solid state water soluble formulation of claim 1, further comprising a fruit extract in an amount of about 5 to about 50 percent by weight with the proviso that any combined amount of fruit extract and green tea extract may not exceed 80 percent by weight of the total formulation.

23. The solid state water soluble formulation of claim 22, wherein said fruit extract is a member selected from the group consisting of: Apples, Apricots, Bananas, Blueberries, Cranberries, Cherries, Figs, Grapes, Grapefruits, Hawthorn berries, Huckleberries, Kiwi fruits, Kumquats, Lemons, Limes, Mangos, Melons, Nectarines, Noni fruit, Oranges, Papayas, Peaches, Pears, Persimmons, Pineapples, Plums, Pomegranates, Raspberries, Strawberries, Tangerines, Watermelons, and mixtures thereof.

24. The solid state water soluble formulation of claim 1, further comprising a vegetable extract in an amount of about 5 to about 50 percent by weight with the proviso that any combined amount of vegetable extract and green tea extract may not exceed 80 percent by weight of the total formulation.

25. The solid state water soluble formulation of claim 24, wherein said vegetable extract is a member selected from the group consisting of: Artichokes, Avocado, Asparagus, Beans, Bell Peppers, Broccoli, Brussel Sprouts, Cabbage, Cauliflower, Carrot, Celery, Cucumber, Eggplant, Green beans, Lettuce, Onions, Parsley, Peas, Potatoes, Pumpkins, Radishes, Radicchio, Rhubarb, Spinach, Tomato, Zucchini, and mixtures thereof.

26. The solid state water soluble formulation of claim 1, wherein said pharmaceutically acceptable acid is a member selected from the group consisting of: food acids, acid anhydrides, acid salts, and mixtures thereof.

27. The solid state water soluble formulation of claim 26, wherein said pharmaceutically acceptable acid is anhydrous citric acid.

28. The solid state water soluble formulation of claim 1, wherein said carbonate salt is a member selected from the group consisting of: sodium carbonate, potassium carbonate, sodium bicarbonate, potassium bicarbonate, sodium glycine carbonate, and mixtures thereof.

29. The solid state water soluble formulation of claim 28, wherein said carbonate salt is sodium bicarbonate.

30. The solid state water soluble formulation of claim 1, wherein said lubricant is a member selected from the group consisting of: sodium benzoate, polyethylene glycols having a molecular weight from about 200 to about 9,000, sodium lauryl sulfate, and mixtures thereof.

31. The solid state water soluble formulation of claim 30, wherein said lubricant is Polyethylene glycol 6000.

32. The solid state water soluble formulation of claim 1, wherein said binder is a member selected from the group consisting of: starches, gelatins, lactose, mannitol, starches, gelatins, lactose, mannitol, acacia, carbomer, carboxymethyl cellulose sodium, dextrin, guar gum, hydroxyethyl cellulose, hydroxypropyl cellulose, hydroxypropylmethyl cellulose, lactose, liquid glucose, maltodextrin, methylcellulose, polymethacrylates, polyvinyl pyrrolidone having a molecular weight range from about 2500 to 3,000,000, and mixtures thereof.

33. The solid state water soluble formulation of claim 32, wherein said binding agent is polyvinyl pyrrolidone.

34. The solid state water soluble formulation of claim 1, further comprising a sweetening agent in an amount of about 0.1 to 5 percent by weight.

35. The solid state water soluble formulation of claim 1, wherein said formulation is a tablet.

36. The solid state water soluble formulation of claim 1, wherein said formulation is granular.

* * * * *